United States Patent [19]
Conley

[11] Patent Number: 5,989,025
[45] Date of Patent: Nov. 23, 1999

[54] DRILL GUIDE

[76] Inventor: Roy Conley, 37 Flat 6 Menuchah, Venachalah, Rehovot Post Code 76247, Israel

[21] Appl. No.: 08/983,295
[22] PCT Filed: May 1, 1997
[86] PCT No.: PCT/IL97/00140
   § 371 Date: Jan. 14, 1998
   § 102(e) Date: Jan. 14, 1998
[87] PCT Pub. No.: WO97/43981
   PCT Pub. Date: Nov. 27, 1997

[30] Foreign Application Priority Data

May 22, 1996 [IL] Israel .......................................... 118371

[51] Int. Cl.⁶ ....................................................... A61C 3/02
[52] U.S. Cl. ........................ 433/76; 408/72 B; 408/241 B
[58] Field of Search ..................... 433/72, 76; 408/72 R, 408/72 B, 115 B, 241 B

[56] References Cited

U.S. PATENT DOCUMENTS

| | | |
|---|---|---|
| 1,189,753 | 7/1916 | Thue . |
| 1,748,006 | 2/1930 | Wohlart ................................ 408/72 B |
| 2,494,229 | 1/1950 | Collison ................................ 408/72 R |
| 2,766,083 | 10/1956 | Fisher ................................... 408/72 R |
| 2,788,684 | 4/1957 | Scharf ................................... 408/72 R |
| 3,224,021 | 12/1965 | Curran .................................. 408/72 B |
| 3,768,918 | 10/1973 | Bethke ................................ 408/241 B |
| 4,445,264 | 5/1984 | Banerian .............................. 408/241 B |
| 5,015,183 | 5/1991 | Fenick . |
| 5,154,548 | 10/1992 | Walsh ................................... 408/72 R |
| 5,320,529 | 6/1994 | Pompa . |
| 5,388,933 | 2/1995 | Dunbar ................................ 408/72 B |
| 5,484,285 | 1/1996 | Morgan et al. ........................ 433/72 |
| 5,556,278 | 9/1996 | Meitner . |

FOREIGN PATENT DOCUMENTS

| | | | |
|---|---|---|---|
| 2399236 | 4/1979 | France ................................... 433/72 |
| 94262200 | 11/1994 | WIPO . |

Primary Examiner—Todd E. Manahan
Assistant Examiner—Eduardo C. Robert
Attorney, Agent, or Firm—Harrison & Egbert

[57] ABSTRACT

A drill guide, for use in the preparation of a dental implant site, having a tubular body with a screw thread along at least a section thereof. The drill guide has a stent with screw threads that are complementary screw threads allow the removable attachment of the tubular body to the stent and allows the axial advancement of the tubular body toward the bone. The complementary screw threads are provided on a matrix material of the stent.

9 Claims, 8 Drawing Sheets

DRILL GUIDE

TECHNICAL FIELD

The present invention relates to a drill guide for use in placement of dental implants. More particularly, the invention provides means for inserting a drill guide into a dental matrix, for use alone or in combination with a wide range of attachments, for drilling, hole enlargement, bone splitting and other purposes.

BACKGROUND ART

Dental implants are used to secure a false tooth or for securing other dental items, such as bridges, in the oral cavity. The aim is to achieve a firm, durable, yet flexible, intra-oral connection to the jaw bone of screw-type or cylinder-type structures made of a biologically compatible material. Such implants are often made of titanium, an alloy thereof, and some have been sprayed with titanium or coated with hydroxyl apatite.

Various forms of dental implants are described in Israel Patents 92360, 92561 and 92564. These specifications do not relate to the problem of drilling an accurate preparatory hole for the insertion therein of the implant.

Briefly, dental implants are inserted in the jaw bone of a patient using the procedure described below:
1. Clinical and radiographic examination.
2. Preparation of a stone model of the relevant existing structures.
3. Preparation of a transparent acrylic stent for use in the mouth during surgery.
4. Bone exposure by incision and dissection of soft tissues.
5. Drilling the bone, using clear acrylic splint as an (imprecise) guide.
6. Hole expansion by further drilling or dilation.
7. Insertion of a screw or cylinder implant.
8. Adding a cover screw or healing cap to the implant head.
9. Stabilizing the tissues to either cover the implant, or to leave the implant cover flush with the gingival tissue.
10. Osseointegration, which takes place naturally during the following 4–12 months.
11. Implant re-exposure, if necessary, and subsequent construction of a dental prosthesis on the implant infrastructure.

When the bone is of small dimensions or is porous, special techniques are used which include bore expansion by hammering in a dilator, increasing bone dimensions by making a chisel fracture, and floor elevation of the maxillary sinus cavity (bone grafting) for increasing the available depth and/or increasing the width by onlay bone or bone-substitute grafting.

Drilling of the bone is carried out by one of the following known techniques: a) free-hand drilling; b) drilling through a prepared hole in a plastic matrix, or c) drilling through a smooth, non-threaded, cylindrical metal drill bush held in a plastic matrix.

The initial hole in the jaw bone must be drilled at the correct location, typically half-way between two existing teeth, at the correct angle in all directions, and to the required depth. A faulty drilling trajectory is very difficult to correct and can cause damage to nearby structures such as the inferior alveolar nerve; it can also cause pain to the patient and, in some cases, cause implant failures.

Free-hand drilling is a technique which is suitable only for the exceptionally skilled and experienced dental surgeon. There will be difficulties when the bone being drilled is not homogeneous, the drill will be deflected and a too-large diameter hole will result.

Technique b) and, to an even greater extent, technique c), greatly reduce the above-mentioned risks associated with free-hand drilling. However, where the guide bore is directly drilled in the plastic matrix as in technique b), play between the bore and the drill is likely to develop, resulting in imperfect results. This problem is overcome in technique c).

The use of a metal drill bush has long been known in production engineering, and standard sizes are commercially available 'off the shelf'. [See Wilson, *Handbook of Fixture Design,* McGraw-Hill Publishers, pp. 15–20 (1962)]. In technique c), this time-tested method is adapted to dental requirements.

However, the non-threaded metal drill bush is difficult to remove from the stent if it needs to be removed and redirected in a corrected drilling axis; furthermore, it is not axially adjustable. Lack of axial adjustment is a disadvantage when drill stability needs improvement, such as when the inner extremity of the bush is spaced from the bone being drilled. In addition, there is no secure means for adding attachments to the bush, such attachments having many important uses, as will be explained further below.

It is therefore an object of the present invention to obviate the disadvantages of the prior art dental implant drilling devices, and to provide a drill guide which is readily removable and replaceable, and which can be prechecked for accuracy.

It is a further object of the present invention to provide a drill guide which is readily depth-adjustable.

It is a still further object of the present invention to provide means for the secure attachment to the drill guide of attachments such as a bush for drilling a pilot hole, holders and guides for dilators and chisel heads, a radiographic marker, a depth gauge, sinus lift attachments, and the like.

Further objects of the invention will become apparent from the following description.

SUMMARY OF THE INVENTION

The present invention achieves the above objectives by providing a drill guide for use in the preparation of a dental implant site, said guide comprising a substantially tubular body having a screw thread along at least a section thereof.

In a preferred embodiment of the invention, there is provided a drill guide having screw threads along at least a lower portion thereof in combination with a stent, wherein said stent is provided with screw threads which are complementary to the screw threads provided on said drill guide, said complementary screw threads enabling the removable attachment of said drill guide to said stent. Through use of a simple tool, it becomes possible to safely remove the drill guide, even during surgery, should it be necessary or advantageous. Removal and replacement of the drill guide is effected without damaging the stent.

In a further preferred embodiment of the present invention, there is provided a drill guide having screw threads along at least an upper section thereof, in combination with an attachment part provided with screw threads which are complementary to the screw threads provided on said drill guide, said complementary threads enabling the removable connection of said attachment part to an upper surface of said drill guide. Various types of attachment parts will be described herein.

Still further embodiments of the invention will be described below.

It will be realized that the novel drill guide of the present invention, which serves during the drilling of a patient's jaw bone, can also be used when a dental model or the patient's mouth is to be drilled.

While the use of the drill guide of the present invention has many advantages, one of the most important and surprising advantages thereof is that, due to the ability to precisely check the drill path before surgery, in combination with the ability to adjust the depth position of the drill bush to contact the patient's gum tissue, it now becomes feasible to drill into the bone without prior surgical exposure thereof. Obviously, the avoidance of surgery on the gingival tissue greatly facilitates the subsequent healing process and is of much benefit to the patient, particularly to elderly patients in whom other health problems are more likely to be coincident. Furthermore, the very fact that such incisions can be avoided may well encourage a patient to accept the proposed treatment. It must be borne in mind that in some countries, it is a legal obligation of the dental surgeon to explain such matters to the patient before commencing treatment.

While the advantages of being able to secure additional attachment parts to the drill guide will be apparent from the following description, some further explanation is required regarding the use of an attachment to improve dilation procedures.

As mentioned above, in step 5 of the implantation procedure, a small diameter pilot hole is drilled into the bone. Thereafter, instead of incremental drilling, dilator pins of gradually increasing diameter are hammered into the pilot hole, which expands by radial compression of the porous bone tissue. The shock of the hammering, which is in itself unpleasant to the patient, may produce an unwanted bone fracture. In addition, further side effects such as bone necrosis and uncontrolled bone fracture may result. The use of a threaded drill guide, however, allows the surgeon to apply a gradual, controlled axial force to advance the dilator in order to expand the hole diameter, thus avoiding hammering and greatly reduce the incidence of unwanted side effects.

A further advantage of the threaded drill guide lies in its more secure attachment to the stent. Consequently, there is a reduced likelihood of the guide coming loose and being swallowed or inhaled by the patient. In addition, attachments which are securely screwed to the guide are less likely to be swallowed or inhaled.

For some operations, a plurality of drill guides is used in a single stent. For example, a stent intended for implantation of a dental implant at the lowest point of the palate will have a drill guide adjacent thereto. Additionally, a second drill guide could be used at a spaced-apart location to drill and insert a screw into the bone, so as to hold the stent firmly in its collect position and to facilitate subsequent accurate drilling of an implant site via the first drill guide.

The invention will now be described in connection with certain preferred embodiments with reference to the following illustrative figures, so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF THE INVENTION

Figure 1:
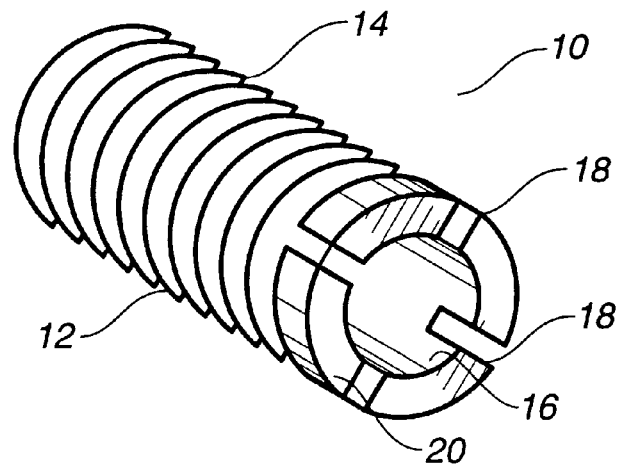
FIG. 1 is a perspective view of a preferred embodiment of the drill guide according to the invention.

There is shown in FIG. 1 a drill guide 10 for use in preparing for the insertion of a dental implant.

In the embodiment of FIG. 1, the guide 10 comprises a tubular body 12 having a male screw thread 14 along its entire length. A useful inner diameter 16 is 2.35 mm, corresponding to the standard dental drill. A pair of cruciate screwdriver slots 18 are seen at the outer extremity 20. Slots 18 allow the application of a torque by either a standard or a Phillips screwdriver (not shown). Drill guide 10 is suitably made of stainless steel, or possibly of certain plastic materials.

With reference to the rest of the drawings, similar reference numerals have been used to identify similar parts.

Figure 2:
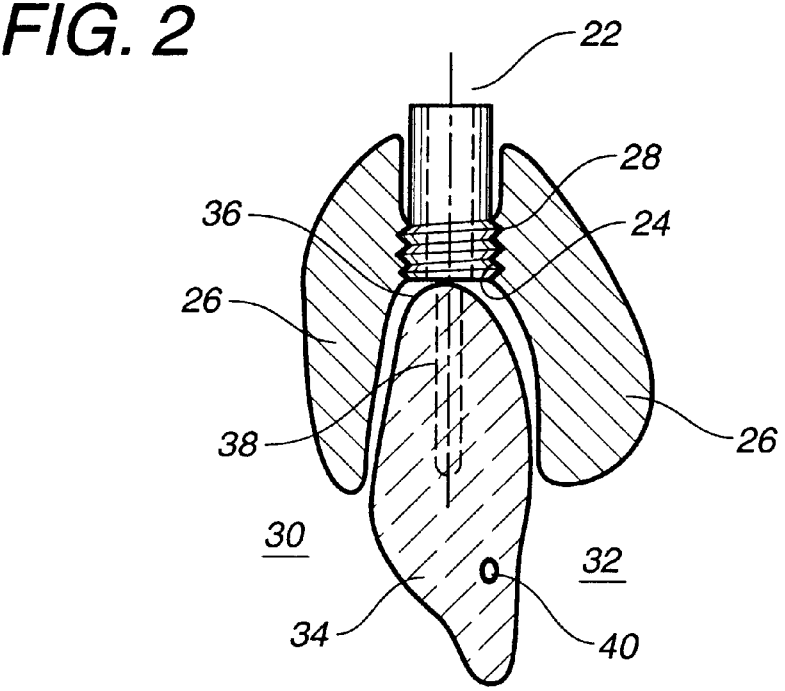
FIG. 2 is a side view of an embodiment of a drill guide held in a dental stent.

Referring now to FIG. 2, there is seen a drill guide 22 having screw threads 24 along its lower portion. Guide 22 is held in a dental stent 26 provided with screw threads 28, which are complementary to screw threads 24. Complementary threads 24, 28 enable the removable attachment of drill guide 22 to stent 26.

The application shown is a tomographic section of the mandible, showing the lingual side 30 and buccal side 32. Since the bone 34 is quite narrow and has a rounded upper surface 36, there is little room for drilling error. The hole 38 being drilled with the aid of drill guide 22 is shown positioned along its correct axis to avoid the inferior alveolar nerve 40.

Figure 3:
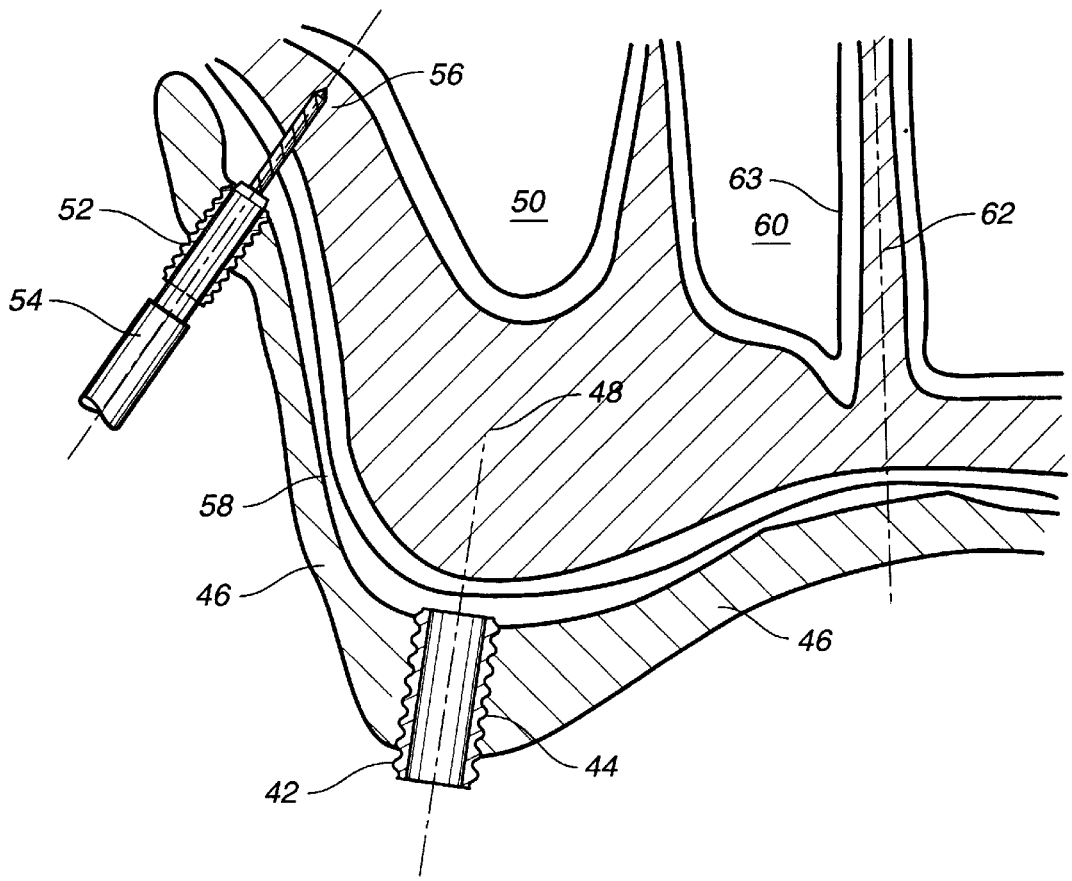
FIG. 3 is a cross-sectional side view of an embodiment where a second drill guide is used to prepare for screw insertion to stabilize a stent in the upper jaw.

FIG. 3 illustrates a further drill guide 42. Complementary screw threads 44 are provided on the matrix material of stent 46. Drill guide 42 is shown against a cross-section of the palate, the implant site 48 being under the maxillary sinus 50. The figure shows a second drill guide 52, being used with a three-tier drill 54. Typical diameters thereof are 2.35 mm. 2 mm and 1.5 mm. After drilling, a temporary holding screw (not shown) will be inserted through the second guide 52 into the patient's jaw bone 56 to hold the stent 46 while the implant site 48 is being prepared. The second guide 52 in this embodiment has an internal diameter of 2 mm.

The bone 56 is covered by soft tissue 58. Above the bone 56 are seen the maxillary sinus 50, nasal cavity 60 and the nasal septum in the midline 62, all lined by mucosae 63.

Figure 4:
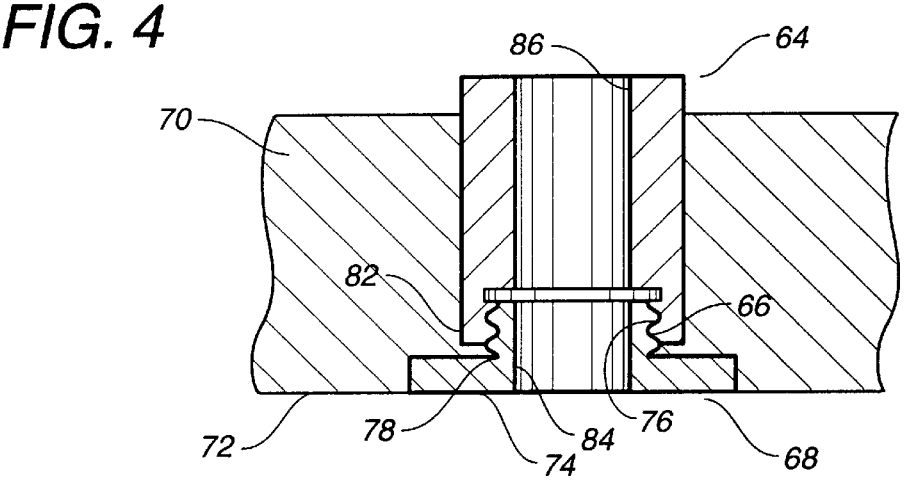
FIG. 4 is a cross-sectional view of an embodiment where the drill guide has an internal thread.

Seen in FIG. 4 is a further embodiment of a drill guide 64 having female screw threads 66 and part 68 attached to the matrix material of stent 70. Part 68, embedded flush with the internal face 72 of stent 70, has a non-cylindrical flange 74 and a male screw thread 76 on its intermediate diameter 78. Drill guide 64 is removably attached by means of complementary female screw thread 66 at its inner end 82. The part 68 has an inner bore 84 equal to, or greater than, the inner diameter 86 of the drill guide 64.

Figure 5:
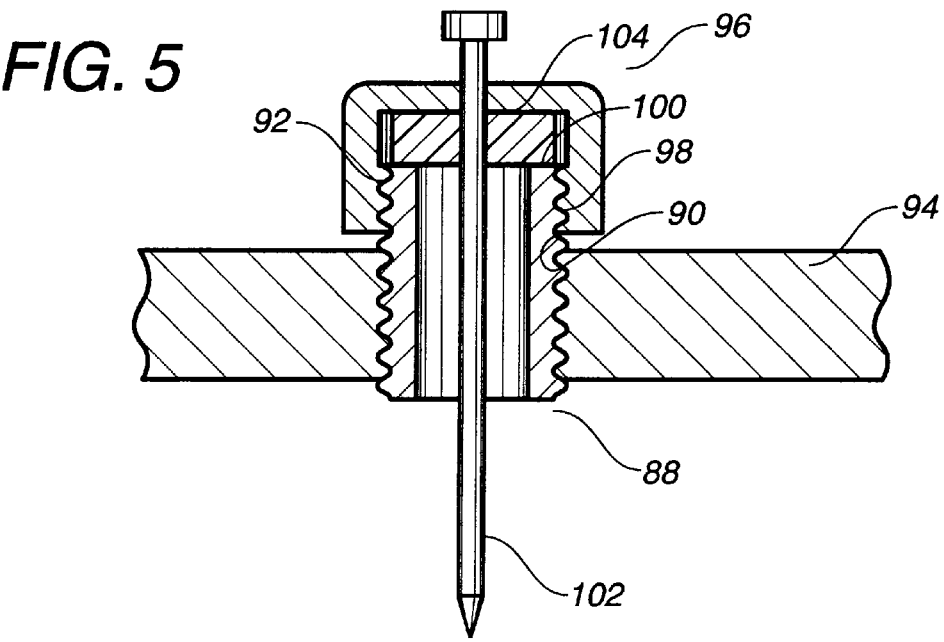
FIG. 5 is a cross-sectional view of an embodiment where the drill guide is used to hold an attachment part.

Referring now to FIG. 5, there is depicted a drill guide 88 having screw threads 90 projecting along an upper section thereof 92, outside the stent 94. Drill guide 88 is used in combination with an attachment part 96 provided with screw threads 98, which are complementary to the screw threads 90 on drill guide 88. Complementary threads 90, 98 enable the removable attachment of a wide variety of attachment parts to the upper surface 100 of drill guide 88. In the embodiment shown, attachment part 96 includes a plastic friction bush 104, which holds different lengths of marker measuring pins 102 and prevents the unintended axial movement thereof.

Figure 6:
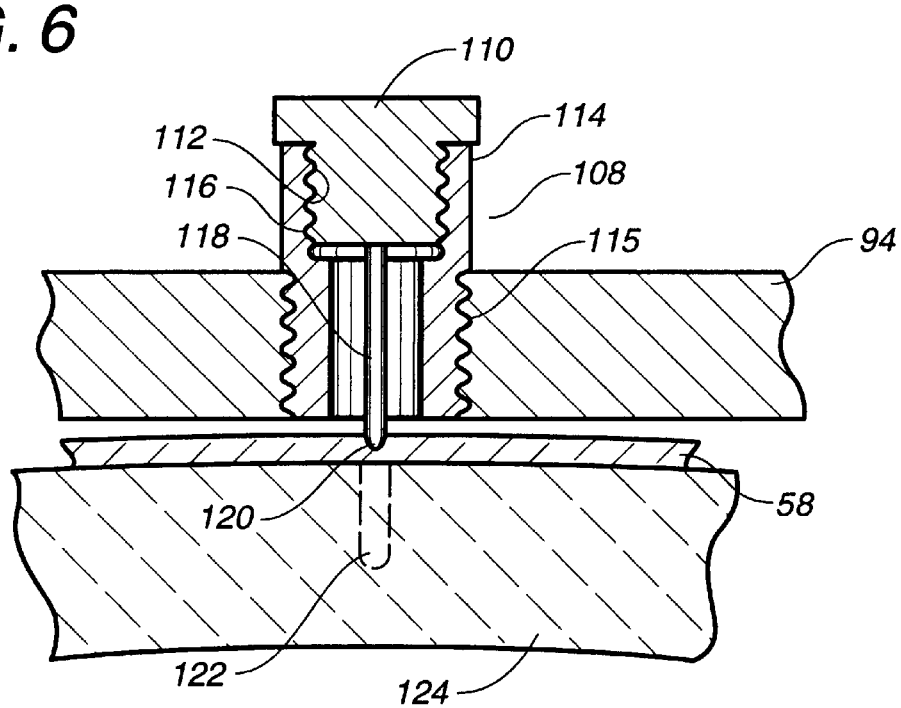
FIG. 6 is a cross-sectional view of an embodiment holding a radiographic marker.

FIG. 6 illustrates a further embodiment of a drill guide 108, also intended to hold an attachment part 110. Drill guide 108 has a female thread 112 near its outer extremity 114 and a male thread 115 along its inner portion. Attachment part 110 has a male screw thread 116; in the depicted embodiment, part 110 comprises a radiographic marker having a length exceeding that of drill guide 108. Pin 118 of the radiographic marker is properly centered, protrudes at the gingival side 120, and provides a clear image, especially when using tomography. Said image aids in determining, with improved accuracy, the central axis 122 of the hole, its position, and its inclination relative to the bone 124.

Figure 7:
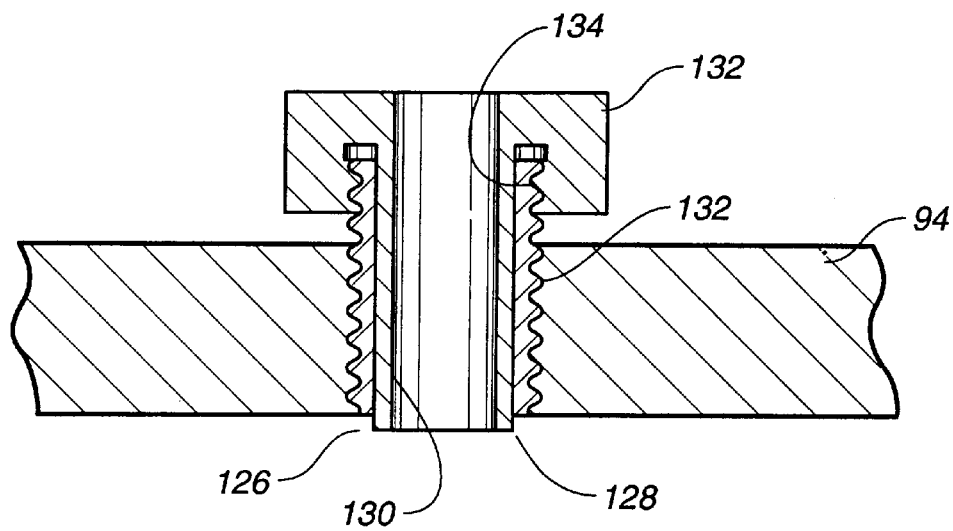
FIG. 7 is a cross-sectional view of an embodiment holding a screwed drill bush used as an internal drill guide.

There is shown in FIG. 7 a drill guide 126 wherein the attachment part comprises a drill bush sleeve 128. Sleeve 128 has an internal bore 130 of a diameter smaller than that of the drill guide 126. Bore 130 guides the drill when preparing a pilot hole, and sleeve 128 is removed as required when a larger hole is to be drilled on exactly the same axis. Bush sleeve head 132 has a female screw thread 134 complementary to the male screw thread 136 of the drill guide 126, and thus secure attachment is provided.

Figure 8:
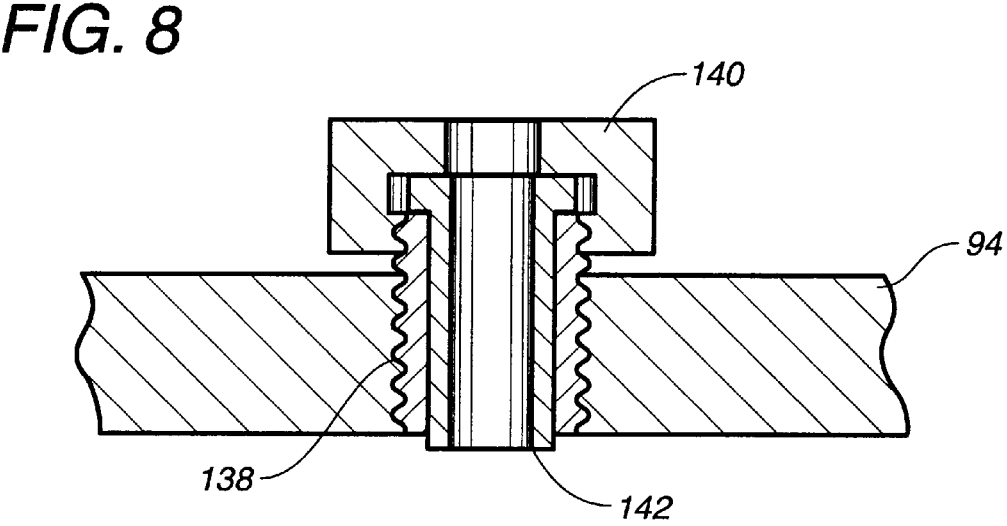
FIG. 8 is a cross-sectional view of an embodiment similar to that shown in FIG. 7, but the internal bush is non-screwed.

With reference to FIG. 8, there is shown a drill guide 138 wherein the attachment part comprises a separate, flanged nut 140. Nut 140 is configured to hold a non-screwed drill bush sleeve 142 in drill guide 138. The embodiment of FIG. 8 is used in a way similar to that of FIG. 7, but it is easier to manufacture.

Figure 9:
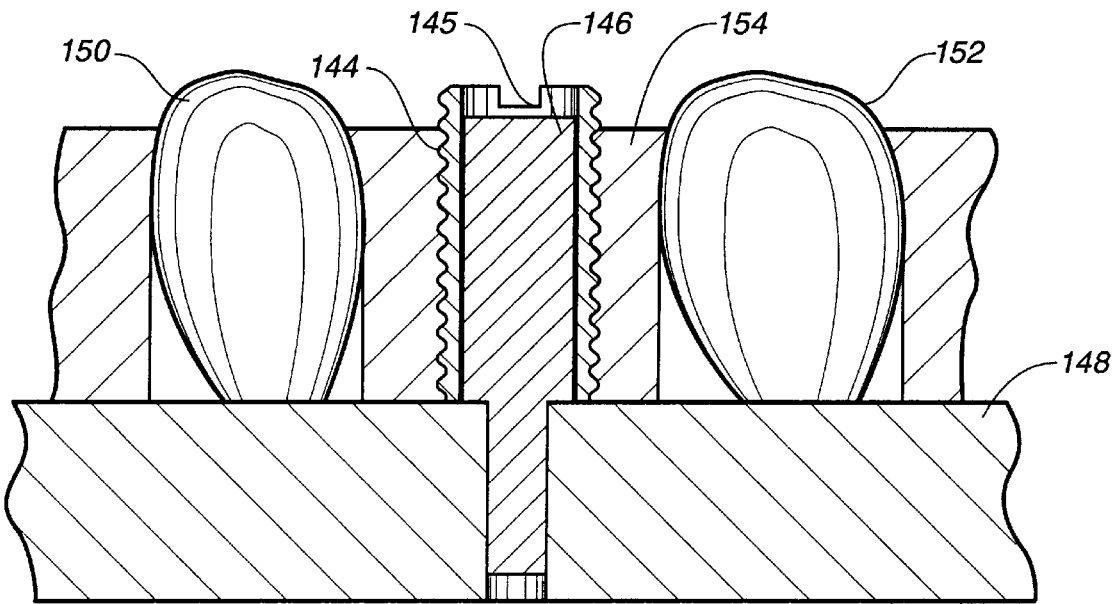
FIG. 9 is a cross-sectional view of an embodiment used in combination with a dental model of the patient's mouth.

FIG. 9 comprises a drill guide 144 wherein the attachment part comprises a guide pin 146, which is slidably inserted without screwing. In the embodiment shown, guide pin 146 is shouldered and is inserted into a dental stone cast 148, shown with adjacent models of teeth 150, 152. Drill guide 144 is inserted over the pin 146 and projects above a matrix material 154, suitably an acrylic resin, which is cast around the model so that the drill guide 144 is securely held in the correct location. Drill guide 144 can be removed by screwing it out; if necessary, using the slot 145.

Figure 10:
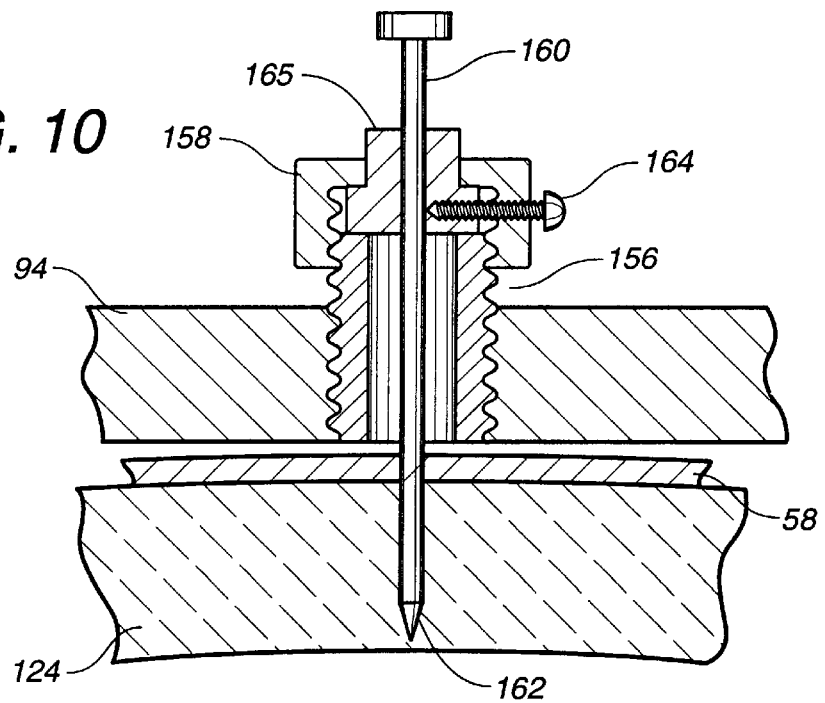
FIG. 10 is a cross-sectional view of an embodiment holding a depth gauge.

There is shown in FIG. 10 a drill guide 156 wherein the attachment part comprises a nut 158, which is used to secure a gauge pin 160 for measuring the depth of a previously drilled hole 162. A side screw 164 secures pin 160 at the measured depth. Measurements are taken directly and with the use of X-rays. The screwed attachment of nut 158 enhances accuracy and patient safety. A shouldered bush 165 is made of a plastic and provides a friction grip to the pin 160, in which case the side screw 164 can be dispensed with.

Figure 11A:
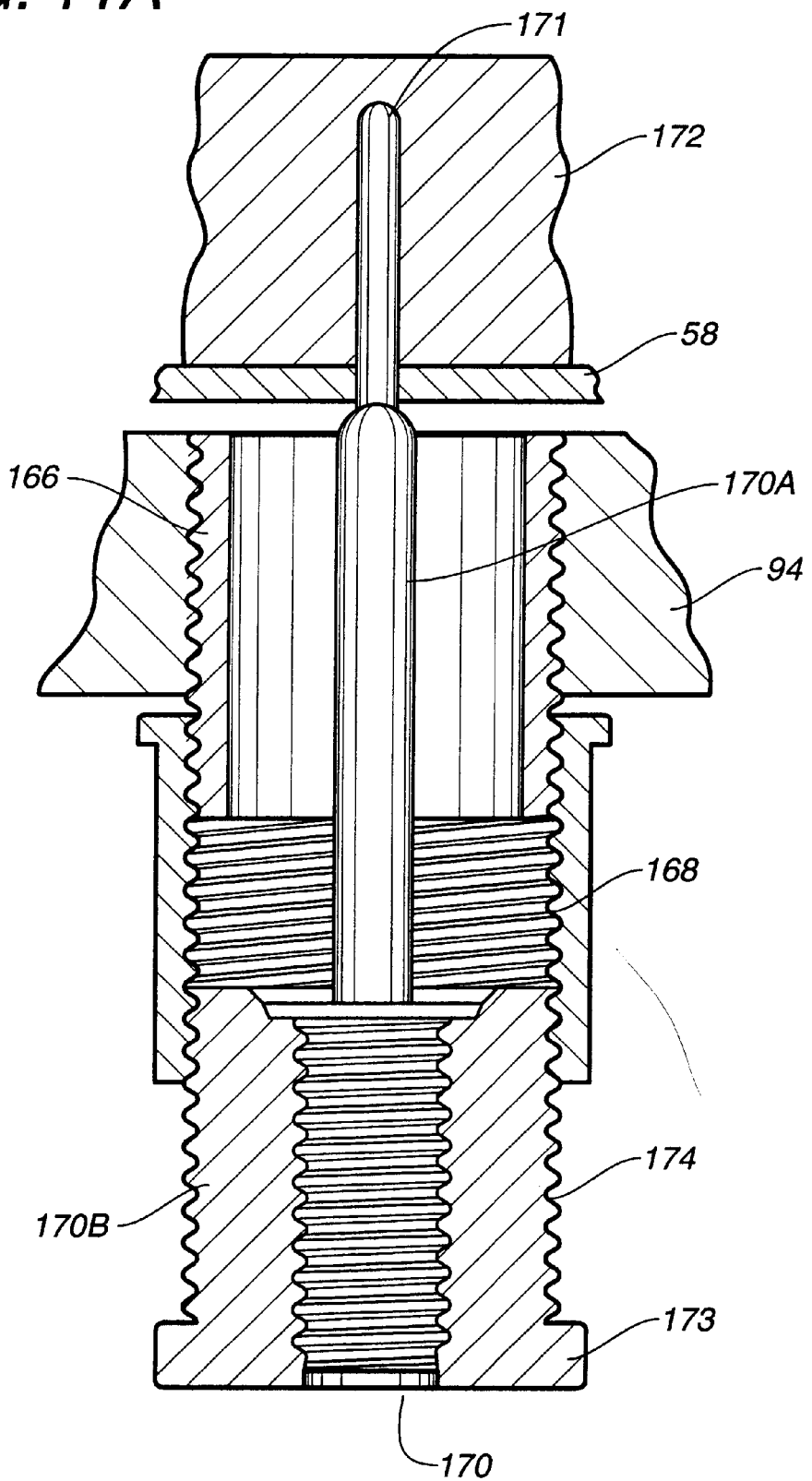
FIG. 11A is a cross-sectional view of an embodiment adapted for use in dilation.

FIG. 11A shows drill guide 166 wherein the attachment part comprises a dilator guide bush 168 for a telescopic dilator 170. The dilator is insertable through the internally-screwed bush 168 and through the drill guide 166, into a pilot hole 171 pre-drilled in a soft, porous bone 172. Dilator 170 has a head 173 configured for the application of a torque by hand tool, or by a motorized tool. By means of screw threads 174, dilator 170 may be advanced at a controlled rate and can easily be retracted.

The telescopic dilator 170 consists of two parts: 170A and 170B. Part 170A is the dilating pin, whose head has a left-hand male thread. Part 170B has a complimentary internal thread to that on the dilating pin 170A, and an external male right-hand thread complimentary to that on guide bush 168. When the dilating pin contacts the smaller diameter pilot hole 171 in the bone, continuing advancement of part 170B causes the pin to extrude from it by virtue of its left-hand thread, thus expanding the soft bone in a controllable manner.

Different configurations of the advancing tip of the dilating pin can have different functions. A rounded tip, as shown in FIG. 11A, is used in implant site expansion in porous bone. A concave or angled tip (not shown) can be used in close sinus lifting procedures to produce a controlled and predictable fracture of the floor of the maxillary sinus and its subsequent elevation with minimal trauma to the mucosal lining. A chiseled-drill guide tip can be used to produce a controlled and predictable bone split.

Guide bush 168 preferably has a geometrical external cross-section, e.g. hexagonal, so that a stabilizing or torquing force can readily be applied thereto.

Telescopic dilator 170 has the advantage of allowing gradual bone expansion and fracture of the maxillary sinus floor and its lifting with or without grafting, but without incisions. In addition, a telescopic configuration is more compact and is therefore space-saving, which is an immense advantage in the mouth, where space limits many procedures.

Figure 11B:
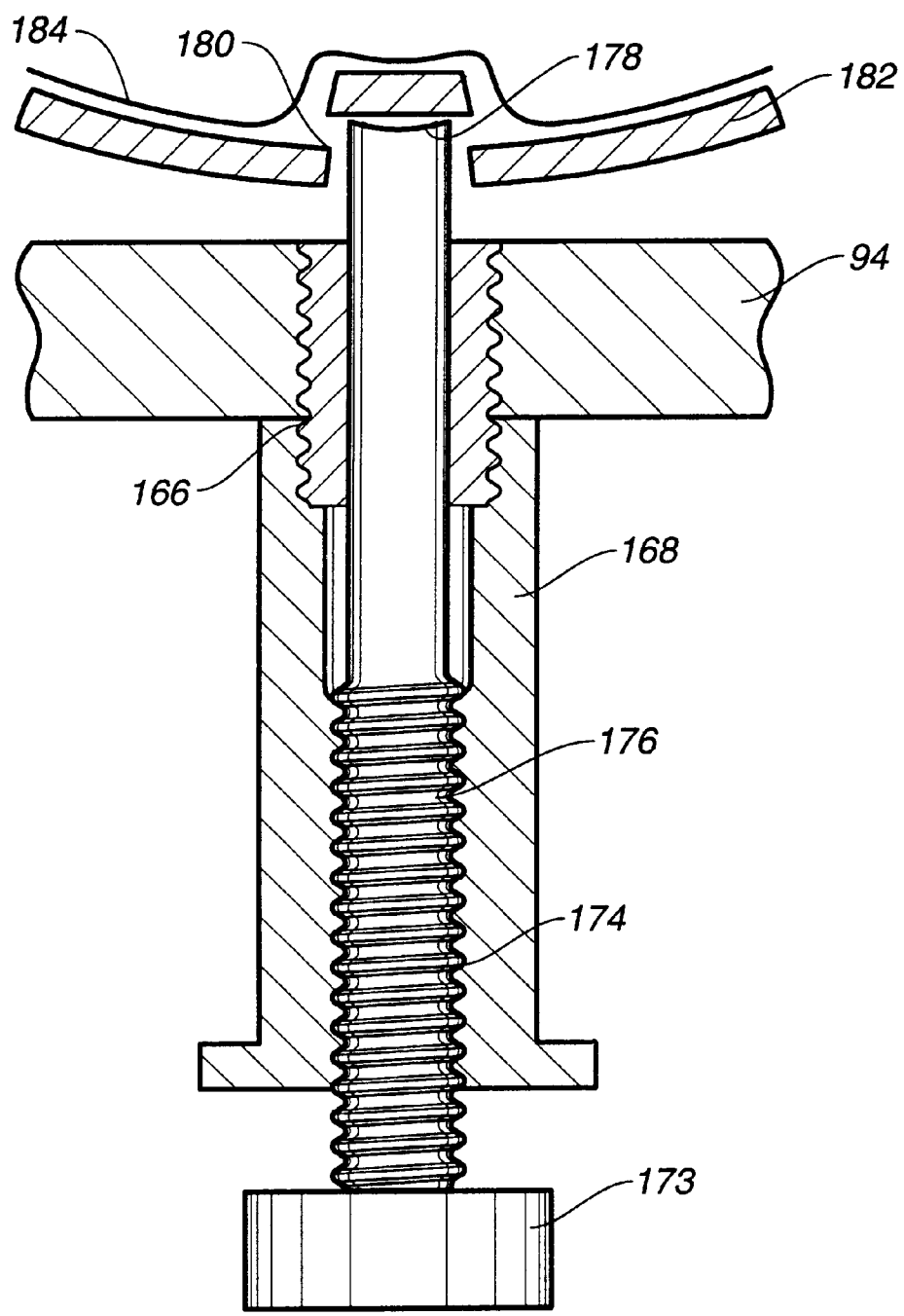
FIG. 11B is similar to FIG. 11A, but shows an embodiment adapted for use as a sinus lift instrument.

FIG. 11B shows a sinus lift instrument 176, having a concave extremity 178. The instrument is used in a manner similar to that of dilator 170, for the purpose of producing a controlled fracture 180 of the sinus floor 182, said fracture having a predictable configuration. The gradual, controlled advance of instrument 176 is made possible by bush 168, the use of which reduces unwanted tearing of the sinus mucosal lining 184. In a further embodiment (not shown), extremity 178 is flat or suitably angled.

Figure 12:
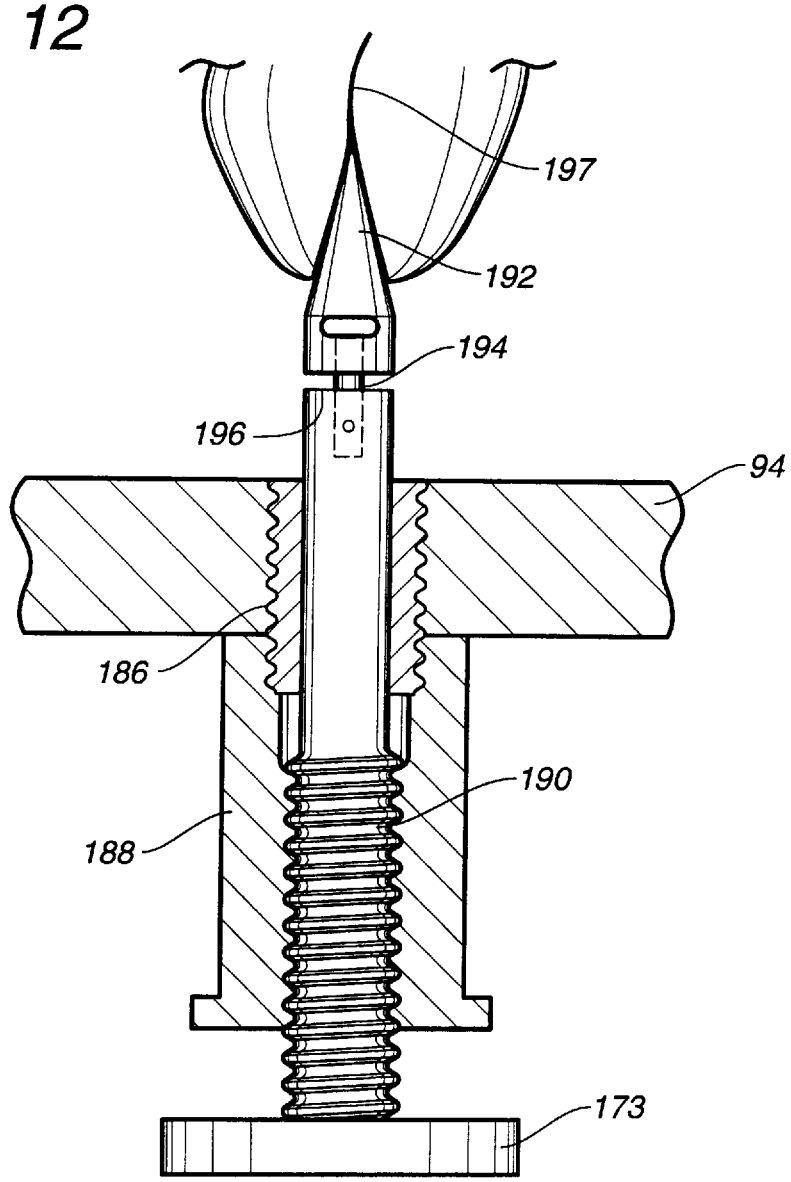
FIG. 12 is a cross-sectional view of an embodiment used in bone splitting.

Referring now to FIG. 12, there is illustrated a drill guide 186 having an attachment part comprising a chisel holder guide bush 188 for chisel holder 190. Chisel holder 190 is screwably advanceable and retractable through the bush 188; chisel head 192 is revolvably attached by an axially-restrained shaft 194 at the inner extremity 196 of holder 190. In operation, chisel head 192 advances without revolving. Its gradual advance makes possible controlled bone splitting, producing a bone fracture 197 in the desired position and no larger than intended.

Figure 13:
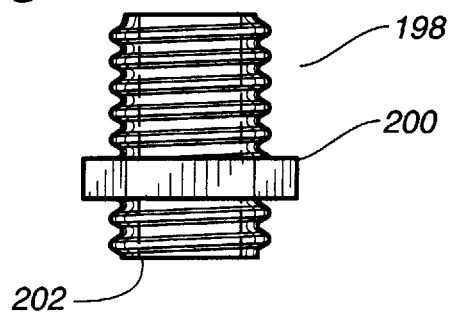
FIG. 13 is an elevational view of a drill guide having a hexagonal sector.

FIG. 13 depicts a drill guide 198 provided with a non-cylindrical sector 200 near its outer extremity 202, which is configured to facilitate the application thereon of a torque. Sector 200 of the embodiment shown is hexagonal; it can be torqued by a suitable tool.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A drill guide apparatus for use in the preparation of a dental implant site, the drill guide comprising:

a substantially tubular body having an external screw thread extending along at least a portion of a length of said tubular body;

a stent formed of a polymeric material, said external screw thread removably engaging said stent, said external screw thread directly contacting said polymeric material of said stent, said tubular body having a portion extending outwardly of a surface of said stent; and an attachment part removably attached to an upper surface of said drill guide, said tubular body having screw threads extending along at least an upper surface of said tubular body, said attachment part provided with screw threads which are complementary to said screw threads of said tubular body, said screw threads of said attachment part enabling the removable attachment of said attachment part to said tubular body, said attachment part is a radiographic marker having a length exceeding that of said tubular body.

2. The drill guide apparatus according to claim 1, said screw thread extending along a lower portion of said tubular body in said stent, said stent being provided with screw threads which are complementary to said screw thread provided on said tubular body, said complementary screw threads enabling the removable engagement of said tubular body to said stent and enabling an axial advancement of said tubular body towards a bone in the dental implant site.

3. The drill guide apparatus according to claim 1, said tubular body provided at an outer extremity thereof with at least one screwdriver slot.

4. The drill guide apparatus of claim 1, said tubular body having a non-cylindrical portion at an end thereof adapted to receive a torque applied by an external tool.

5. The drill guide apparatus of claim 1, said screw thread extending along an entire length of said tubular body.

6. A drill guide apparatus for use in the preparation of a dental implant site, the drill guide comprising:

a substantially tubular body having an external screw thread extending along at least a portion of a length of said tubular body;

a stent formed of a polymeric material, said external screw thread removably engaging said stent, said external screw thread directly contacting said polymeric material of said stent, said tubular body having a portion extending outwardly of a surface of said stent; and an attachment part removably attached to an upper surface of said drill guide, said tubular body having screw threads extending along at least an upper surface of said tubular body, said attachment part provided with screw threads which are complementary to said screw threads of said tubular body, said screw threads of said attachment part enabling the removable attachment of said attachment part to said tubular body, said attachment part is a flanged nut configured to hold a non-screwed drill guide bush sleeve in said tubular body.

7. A drill guide apparatus for use in the preparation of a dental implant site, the drill guide comprising:

a substantially tubular body having an external screw thread extending along at least a portion of a length of said tubular body;

a stent formed of a polymeric material, said external screw thread removably engaging said stent, said external screw thread directly contacting said polymeric material of said stent, said tubular body having a portion extending outwardly of a surface of said stent; and an attachment part removably attached to an upper surface of said drill guide, said tubular body having screw threads extending along at least an upper surface of said tubular body, said attachment part provided with screw threads which are complementary to said screw threads of said tubular body, said screw threads of said attachment part enabling the removable attachment of said attachment part to said tubular body, wherein said attachment part is a guide bush and a dilator, said dilator being insertable through said guide bush and through said tubular body.

8. A drill guide apparatus for use in the preparation of a dental implant site, the drill guide comprising:

a substantially tubular body having an external screw thread extending along at least a portion of a length of said tubular body;

a stent formed of a polymeric material, said external screw thread removably engaging said stent, said external screw thread directly contacting said polymeric material of said stent, said tubular body having a portion extending outwardly of a surface of said stent; and an attachment part removably attached to an upper surface of said drill guide, said tubular body having screw threads extending along at least an upper surface of said tubular body, said attachment part provided with screw threads which are complementary to said screw threads of said tubular body, said screw threads of said attachment part enabling the removable attachment of said attachment part to said tubular body, wherein said attachment part is a guide bush and a chisel holder, said chisel holder being screwably advanceable and retractable through said guide bush, said chisel holder having a head of a chisel revolvably attached to an inner extremity of said chisel holder.

9. A drill guide apparatus for use in the preparation of a dental implant site, the drill guide comprising:

a substantially tubular body having an external screw thread extending along at least a portion of a length of said tubular body;

a stent formed of a polymeric material, said external screw thread removably engaging said stent, said external screw thread directly contacting said polymeric material of said stent, said tubular body having a portion extending outwardly of a surface of said stent; and an attachment part removably attached to an upper surface of said drill guide, said tubular body having screw threads extending along at least an upper surface of said tubular body, said attachment part provided with screw threads which are complementary to said screw threads of said tubular body, said screw threads of said attachment part enabling the removable attachment of said attachment part to said tubular body, wherein said attachment part comprises a telescopic dilator.

* * * * *